US011560420B2

(12) United States Patent
Ritter et al.

(10) Patent No.: US 11,560,420 B2
(45) Date of Patent: Jan. 24, 2023

(54) METHOD FOR PRODUCING ANTIBODIES USING OVINE B-CELLS AND USES THEREOF

(71) Applicant: Roche Diagnostics Operations, Inc., Indianapolis, IN (US)

(72) Inventors: Mirko Ritter, Bernried (DE); Styliani Tournaviti, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/017,043

(22) Filed: Jun. 25, 2018

(65) Prior Publication Data

US 2018/0305441 A1 Oct. 25, 2018

Related U.S. Application Data

(63) Continuation of application No. 14/946,957, filed on Nov. 20, 2015, now abandoned, which is a continuation of application No. PCT/EP2014/060202, filed on May 19, 2014.

(30) Foreign Application Priority Data

May 21, 2013 (EP) ..................................... 13168590

(51) Int. Cl.
*C07K 16/00* (2006.01)
*C12N 5/00* (2006.01)

(52) U.S. Cl.
CPC .......... *C07K 16/00* (2013.01); *C07K 2317/20* (2013.01)

(58) Field of Classification Search
None
See application file for complete search history.

(56) References Cited

U.S. PATENT DOCUMENTS

| | | | |
|---|---|---|---|
| 5,010,182 A | 4/1991 | Brake et al. | |
| 5,540,926 A | 7/1996 | Aruffo et al. | |
| 6,020,170 A | 2/2000 | Steenbakkers | |
| 2006/0051348 A1 | 3/2006 | Gorlach | |
| 2007/0269868 A1 | 11/2007 | Carvalho Jensen et al. | |
| 2009/0275056 A1 | 11/2009 | Lawson et al. | |
| 2014/0302559 A1 | 10/2014 | Hoege et al. | |
| 2015/0087533 A1 | 3/2015 | Hoogenboom et al. | |
| 2016/0222112 A1 | 8/2016 | TenHoor et al. | |
| 2019/0136185 A1* | 5/2019 | Tedder | A61K 35/17 |

FOREIGN PATENT DOCUMENTS

| | | |
|---|---|---|
| EP | 0222360 A2 | 11/1986 |
| EP | 0362179 A2 | 8/1989 |
| JP | H01-171494 A | 7/1989 |
| WO | 1999/42077 A2 | 8/1999 |
| WO | 2001/90316 A2 | 11/2001 |
| WO | 2004/078782 A1 | 9/2004 |
| WO | 2005/121789 A1 | 12/2005 |
| WO | 2007/031550 A2 | 3/2007 |
| WO | 2007/067410 A2 | 6/2007 |
| WO | 2007/124299 A2 | 11/2007 |
| WO | 2011/085247 A2 | 7/2011 |
| WO | 2013/076139 A1 | 5/2013 |

OTHER PUBLICATIONS

Van den Broeke et al (J of Virology, 2001, v.75,pp. 1095-1103.*
Kiener et al. (J of Virology, 2006, v.80, pp. 1922-1938.*
Abe et al ., J of Immunolog.Method, 1986, v.90 pp. 111-123.*
Maurer et al., Cell Immunol, 1983, v. 79 pp. 36-43.*
Chothia, Cyrus and Lesk, Arthur M., Canonical Structures for the Hypervariable Regions of Immunoglobulins, Journal of Molecular Biology, 1987, pp. 901-917, vol. 196.
Clackson, Tim et al., Making antibody fragments using phage display libraries, Nature, 1991, pp. 624-628, vol. 352.
Griebel, Philip et al., CD40 signaling induces B cell responsiveness to multiple members of the γ chain-common cytokine family, International Immunology, 1999, pp. 1139-1147, vol. 11, No. 7.
Griebel, Philip J. et al., Cloning non-transformed sheep B cells, Journal of Immunological Methods, 2000, pp. 19-28, vol. 237.
International Search Report dated Oct. 7, 2014 in Application No. PCT/EP2014-060202, 4 pages.
Kwekkeboom, Jaap et al., An efficient procedure for the generation of human monoclonal antibodies based on activation of human B lymphocytes by a murine thymoma cell line, Journal of Immunological Methods, 1993, pp. 117-127, vol. 160.
MacCallum, Robert M. et al., Antibody-antigen Interactions: Contact Analysis and Binding Site Topography, Journal of Molecular Biology, 1996, pp. 732-745, vol. 262.
Miyasaka, M. and Dudler, L., Differentiation of Ovine Immature B Cells upon Exposure to Phorbol Myristate Acetate, International Archives of Allergy and Applied Immunology, 1984, pp. 281-283, vol. 74.
Miyasaka, M. et al., Differentiation of B lymphocytes in sheep, Immunology, 1984, pp. 515-523, vol. 53.
Morgan, David O. et al., Antibody-Induced Down-Regulation of a Mutated Insulin Receptor Lacking an Intact Cytoplasmic Domain, Biochemistry, 1987, pp. 2959-2963, vol. 26, No. 11.
Néron, Sonia et al., Tuning of CD40-CD154 Interactions in Human B-Lymphocyte Activation: A Broad Array of In Vitro Models for a Complex In Vivo Situation, Archivum Immunologiae et Therapiae Experimentallis, 2011, pp. 25-40, vol. 59, No. 1.
Osborne, Jennifer et al., Novel Super-High Affinity Sheep Monoclonal Antibodies Against CEA Bind Colon and Lung Adenocarcinoma, 1999, pp. 183-191, vol. 18, No. 2.
Pak, S. C. O. et al., Super-CHO—A cell line capable of autocrine growth under fully defined protein-free conditions, Cytotechnology, 1996, pp. 139-146, vol. 22.

(Continued)

*Primary Examiner* — Michail A Belyavskyi
(74) *Attorney, Agent, or Firm* — Stinson LLP

(57) ABSTRACT

Herein is reported a cultivation system for cultivating a pool of ovine B-cells or single deposited ovine B-cells in the presence of phorbol myristate acetate (PMA).

5 Claims, 3 Drawing Sheets

(56) References Cited

OTHER PUBLICATIONS

Paus, Didrik et al., Antigen recognition strength regulates the choice between extrafollicular plasma cell and germinal center B cell differentiation, The Journal of Experimental Medicine, 2006, pp. 1081-1091, vol. 203, No. 4.

Portolano, Stefano, Lack of Promiscuity in Autoantigen-Specific H and L Chain Combinations as Revealed by Human H and L Chain "Roulette", The Journal of Immunology, 1993, pp. 880-887, vol. 150, No. 3.

Ralph, Peter and Kishimoto, Tadamitsu, Tumor Promoter Phorbol Myristic Acetate Stimulates Immunoglobulin Secretion Correlated with Growth Cessation in Human B Lymphocyte Cell Lines, Journal of Clinical Investigation, 1981, pp. 1093-1096, vol. 68.

Sedgmen, Bradley J. et al., Optimization of an ovine antibody-secreting cell assay for detection of antigen-specific immunoglobulin production in peripheral blood, Immunology and Cell Biology, 2003, pp. 305-310, vol. 81.

Smith, Kenneth G. C. et al., The extent of affinity maturation differs between the memory and antibody-forming cell compartments in the primary immune response, The EMBO Journal, 1997, pp. 2996-3006, vol. 16, No. 11.

Spieker-Polet, Helga et al., Rabbit monoclonal antibodies: Generating a fusion partner to product rabbit-rabbit hybridomas, Proceedings of the National Academy of Sciences USA, 1995, pp. 9438-9352, vol. 92.

Weitkamp, Jörn-Hendrik et al., Generation of recombinant human monoclonal antibodies to rotavirus from single antigen-specific B cells selected with fluorescent virus-like particles, Journal of Immunological Methods, 2003, pp. 223-237, vol. 275.

Wrammert, Jens et al., Rapid cloning of high-affinity human monoclonal antibodies against influenza virus, Nature, 2008, pp. 667-672, vol. 453.

Zubler, Rudolf H. et al., Activated B Cells Express Receptors For, and Proliferate in Response To, Pure Interleukin 2, The Journal of Experimental Medicine, 1984, pp. 1170-1183, vol. 160.

Zubler, Rudolf H., Polyclonal B cell responses in the presence of defined filler cells: complementary effects of lipopolysaccharide and anti-immunoglobulin antibodies, European Journal of Immunology, 1984, pp. 357-363, vol. 14.

Ghamlouch, Hussein et al., Phorbol myristate acetate, but not CD40L, induces the differentiation of CLL B cells into Ab-secreting cells, Immunology and Cell Biology, 2014, pp. 591-604, vol. 92.

* cited by examiner

METHOD FOR PRODUCING ANTIBODIES USING OVINE B-CELLS AND USES THEREOF

This application is a continuation of U.S. application Ser. No. 14/946,957 filed Nov. 20, 2015 (now abandoned), which is a continuation of International Patent Application No. PCT/EP2014/060202 filed May 19, 2014, and claims priority to European Patent Application No. 13168590.1 filed May 21, 2013, the disclosures of which are hereby incorporated by reference in their entirety.

The current patent application is in the field of B-cell cultivation. Herein is reported a culture system for stimulation and expansion of sheep derived antibody-secreting cells, such as activated B-cells, plasmablasts and B-cells isolated from immunized sheep in the presence of phorbol myristate acetate.

BACKGROUND OF THE INVENTION

It has been reported that isolated B-cells, plasmablasts and plasma cells from different species were difficult to culture in vitro. In practice this is normally overcome by the generation of immortal B-cell lines by fusing primary B-cells to a hybridoma partner or immortalization. For rabbits also a plasmacytoma fusion partner was developed (Spieker-Polet, H., et. al., Proc. Natl. Acad. Sci. USA 92 (1995) 9348-9352, but the hybridoma technique does not work well in rabbits. For sheep the hybridoma technology has also been described (see e.g. Osborne, J., et al., Hybridoma 18 (1999) 183-191) but also these hybridomas tend to be instable and have poor productivities. For sustained survival of B-cells in vitro it is necessary to provide essential activation stimuli and survival factors. A variety of compounds have been described such as IL-2, IL-4, IL-10 and others (see e.g. Zubler, R., et al., Eur. J. Immunol. 14 (1984) 357-363, and J. Exp. Med. 160 (1984) 1170-1183).

Physiologically, B-cells are activated upon encounter with a specific antigen plus additional activation e.g. via the CD40/CD40L pathway (reviewed in Néron, S., et al., Arch. Immunol. Ther. Exp. 59 (2011) 25-40) and/or via cytokines and/or growth factors derived from the natural context, e.g. by Dendritic cells or upon T-cell help.

In in vitro systems the CD40/CD40L interaction can be mimicked by co-culture with EL4-B5 thymoma cells or the addition of soluble or immobilized anti-CD40 antibodies or CD40L. The sole systems lack sufficient potency and are only described in combination with further required stimuli using either different feeder mixes (e.g. Zubler mix; IL-4, IL-10, etc.) (Zubler, R., supra) or thymocyte supernatant (TSN).

Weitkamp, J-H., et al., (J. Immunol. Meth. 275 (2003) 223-237) report the generation of recombinant human monoclonal antibodies to rotavirus from single antigen-specific B-cells selected with fluorescent virus-like particles. A method of producing a plurality of isolated antibodies to a plurality of cognate antigens is reported in US 2006/0051348. A culture method for obtaining a clonal population of antigen-specific B-cells is reported in US 2007/0269868. A method for preparing immunoglobulin libraries is reported in WO 2007/031550.

Griebel, P. J., et al. Report the cloning non-transformed sheep B cells (J. Immunol. Meth. 237 (2000) 19-28). CD40 signaling induces B cell responsiveness to multiple members of the gamma chain-common cytokine family is reported by Griebel, P., et al. (Int. Immunol. 11 (1999) 1139-1147). Miyasaka, M. and Dudler, L., report the Differentiation of ovine immature B cells upon exposure to phorbol myristate acetate (Int. Arch. Allergy Appl. Immunol. 74 (1984) 281-283). Differentiation of B lymphocytes in sheep: I. Phenotypic analysis of ileal Peyer's patch cells and the demonstration of a precursor population for slg+ cells in the ileal Peyer's patches is reported by Miyasaka, M., et al. (Immunol. 53 (1984) 515-523). Sedgmen, B. J., et al. report the optimization of an ovine antibody-secreting cell assay for detection of antigen-specific immunoglobulin production in peripheral blood leukocytes (Immunol. Cell Biol. 81 (2003) 305-310).

SUMMARY OF THE INVENTION

Herein is reported a new method for the rapid, efficient and reproducible generation of ovine antibodies starting from ovine B-cells and comprising at least one cultivation step.

Herein is further reported the use of phorbol myristate acetate (PMA) as additive for the cultivation of ovine B-cells to provide a highly efficient ovine B-cell stimulation and cultivation system.

One aspect as reported herein is a method for cultivating ovine B-cells in the presence of/together with phorbol myristate acetate (PMA).

One aspect as reported herein is a method for cultivating ovine B-cells in the presence of/together with phorbol myristate acetate (PMA), ovine TSN and feeder cells.

One aspect as reported herein is a method for co-cultivating ovine B-cells and feeder cells in the presence of/together with phorbol myristate acetate (PMA).

One aspect as reported herein is a method for producing an ovine antibody comprising the step of cultivating an antibody secreting ovine B-cell in the presence of/together with phorbol myristate acetate (PMA) and recovering the antibody from the cultivation supernatant, thereby producing the ovine antibody.

In one embodiment the ovine B-cell is a naive or non-mature ovine B-cell.

In one embodiment the B-cell is an IgG positive B-cell ($IgG^+$). IgG positive B-cells present the cell surface marker IgG which can be detected and labeled.

In one embodiment the B-cell is an IgG positive and CD45R positive B-cell ($IgG^+CD45R^+$). IgG positive B-cells present the cell surface marker IgG which can be detected and labeled.

In one embodiment the B-cell is an IgG positive and CD21 positive B-cell ($IgG^+CD21^+$). IgG positive B-cells present the cell surface marker IgG which can be detected and labeled.

One aspect as reported herein is a method for producing an antibody, which specifically binds to an antigen, comprising the following steps:
 a) cultivating a pool of or a single deposited antibody secreting ovine B-cell in the presence/together with phorbol myristate acetate (PMA),
 b) isolating a nucleic acid encoding the amino acid sequence of the variable light chain domain and isolating a nucleic acid encoding the amino acid sequence of the variable heavy chain domain of an antibody, which specifically binds to an antigen,
 c) cultivating a cell comprising the nucleic acid isolated in b) or a variant thereof encoding a humanized version of the light and/or heavy chain variable domain within one or more expression cassettes, d) recovering the antibody from the cell or the cultivation medium and thereby producing an antibody, which specifically binds to an antigen.

In one embodiment the method comprises the following steps:
a) providing a population of antibody secreting (mature) B-cells (obtained from the blood of a sheep),
b) staining the cells of the population of B-cells with at least one fluorescence dye (in one embodiment with one to three, or two to three fluorescence dyes),
c) depositing single cells of the stained population of B-cells or a pool of cells from the stained population of B-cells in individual containers (in one embodiment is the container a well of a multi well plate),
d) cultivating the deposited individual B-cells in the presence of phorbol myristate acetate (PMA),
e) determining the binding specificity of the antibodies secreted in the cultivation of the individual or pool of B-cells,
f) determining the amino acid sequence of the variable light and heavy chain domain of specifically binding antibodies by a reverse transcriptase PCR and nucleotide sequencing, and thereby obtaining a monoclonal antibody variable light and heavy chain domain encoding nucleic acid,
g) introducing the monoclonal antibody light and heavy chain variable domain encoding nucleic acid in an expression cassette for the expression of an antibody,
h) introducing the nucleic acid in a cell,
i) cultivating the cell and recovering the antibody from the cell or the cell culture supernatant and thereby producing an antibody, which specifically binds to an antigen.

In one embodiment the method comprises the following steps:
a) providing a population of antibody secreting (mature) sheep B-cells,
b) staining the cells of the population of ovine B-cells with at least one fluorescence dye (in one embodiment with one to three, or two to three fluorescence dyes),
c) depositing single cells of the stained population of ovine B-cells or a pool of cells from the stained population of ovine B-cells in individual containers (in one embodiment is the container a well of a multi well plate),
d) cultivating the deposited ovine B-cells in the presence of phorbol myristate acetate (PMA),
e) determining the binding specificity of the antibodies secreted in the cultivation of the ovine B-cells,
f) determining the amino acid sequence of the variable light and heavy chain domain of specifically binding antibodies by a reverse transcriptase PCR and nucleotide sequencing, and thereby obtaining a monoclonal antibody variable light and heavy chain domain encoding nucleic acid,
g) introducing the monoclonal antibody light and heavy chain variable domain encoding nucleic acid in an expression cassette for the expression of an antibody,
h) introducing the nucleic acid in a cell,
i) cultivating the cell and recovering the antibody from the cell or the cell culture supernatant and thereby producing an antibody, which specifically binds to an antigen.

In one embodiment the pool of cells comprises of from about 10 B-cells to about 1,000,000 B-cells. In one embodiment the pool comprises of from about 500 B-cells to about 100,000 B-cells. In one embodiment the pool comprises about 500 B-cells.

One aspect as reported herein is the use of phorbol myristate acetate (PMA) in the cultivation of antibody secreting ovine B-cells.

One aspect as reported herein is a method for cultivating ovine B-cells comprising the step of cultivating a single deposited ovine B-cell or a pool of ovine B-cells together with/in the presence of phorbol myristate acetate (PMA).

One aspect as reported herein is the use of phorbol myristate acetate (PMA) in a cultivation of an ovine B-cell for improving cell growth.

One aspect as reported herein is a method for improving cell growth of ovine B-cells comprising the step of cultivating a single deposited ovine B-cell or a pool of ovine B-cells together with/in the presence of phorbol myristate acetate (PMA).

DETAILED DESCRIPTION OF THE INVENTION

Figure 1:
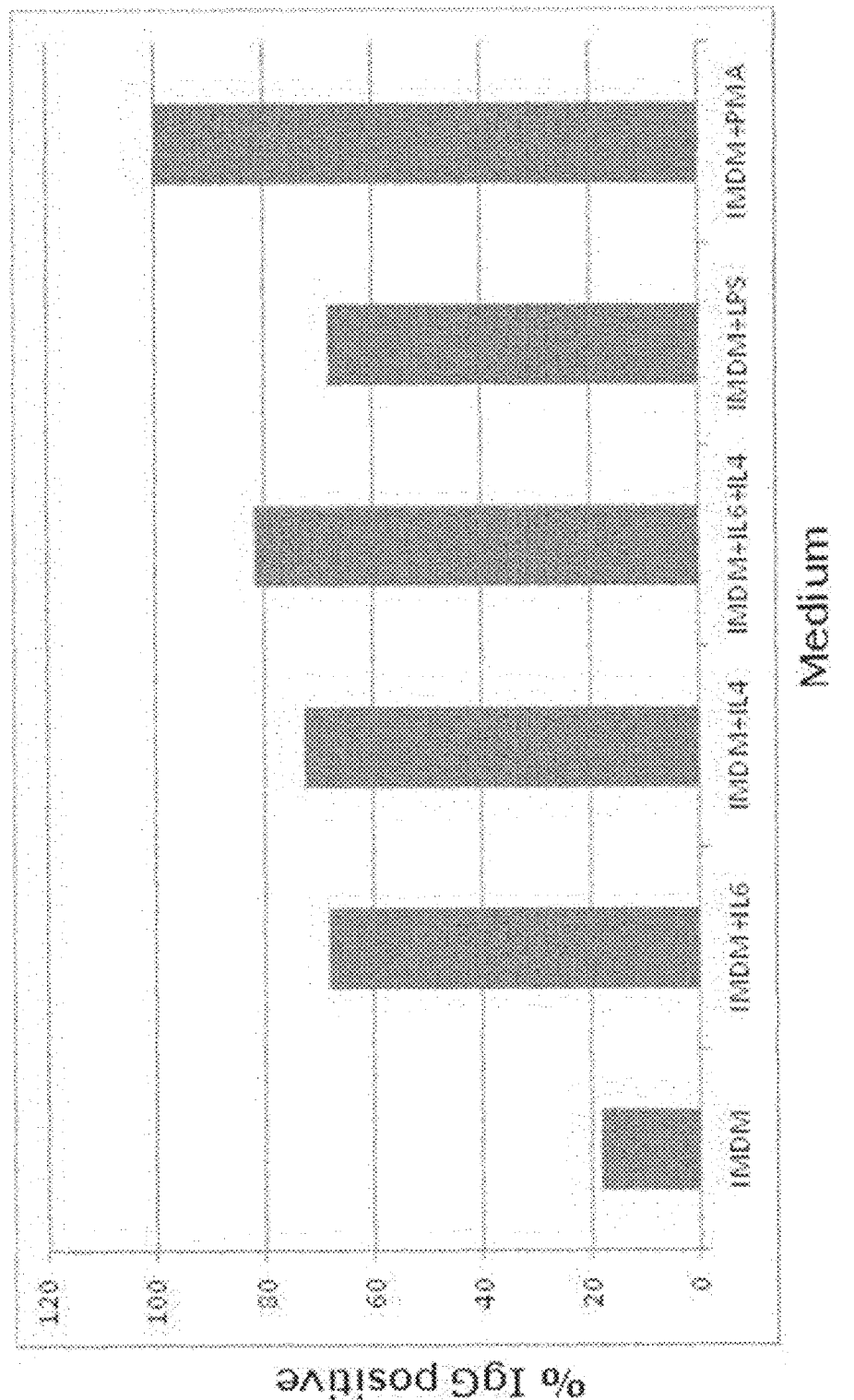
FIG. 1 IgG secretion by in vitro cultivated sIgG$^+$CD45R$^+$ B-cells.

The subject matter reported herein provides a generally applicable method for the rapid, efficient and reproducible generation of ovine, chimeric (i.e. ovine-non-ovine species chimeric), or humanized antibodies starting from ovine B-cells and comprising at least one cultivation step. It has been found that the addition of phorbol myristate acetate (PMA) to the cultivation medium can improve the growth characteristics of ovine B-cells, i.e. the ovine B-cells, either a single deposited cell or as pool of cells, can be grown more rapidly to high cell densities than in the absence of phorbol myristate acetate (PMA). Thus, it is possible to obtain high ovine B-cell densities and correspondingly high IgG concentrations in the cultivation supernatant in short time.

One aspect as reported herein is a method for cultivating ovine B-cells in the presence of/together with phorbol myristate acetate (PMA).

One aspect as reported herein is a method for cultivating ovine B-cells in the presence of/together with phorbol myristate acetate (PMA), ovine TSN and feeder cells.

One aspect as reported herein is a method for co-cultivating ovine B-cells and feeder cells in the presence of/together with phorbol myristate acetate (PMA).

One aspect as reported herein is a method for producing an ovine antibody comprising the step of cultivating an antibody secreting ovine B-cell in the presence of/together with phorbol myristate acetate (PMA) and recovering the antibody from the cultivation supernatant, thereby producing the ovine antibody.

One aspect as reported herein is a method for producing an antibody, which specifically binds to an antigen, comprising the following steps:
a) cultivating a pool of or a single deposited antibody secreting ovine B-cell in the presence/together with phorbol myristate acetate (PMA),
b) isolating a nucleic acid encoding the amino acid sequence of the variable light chain domain and isolating a nucleic acid encoding the amino acid sequence of the variable heavy chain domain of an antibody, which specifically binds to an antigen, c) cultivating a cell comprising the nucleic acid isolated in b) or a variant thereof encoding a humanized version of the light and/or heavy chain variable domain within one or more expression cassettes, d) recovering the antibody from the cell or the cultivation medium and thereby producing an antibody, which specifically binds to an antigen.

One aspect as reported herein is the use of phorbol myristate acetate (PMA) in the cultivation of antibody secreting ovine B-cells.

One aspect as reported herein is a method for cultivating ovine B-cells comprising the step of cultivating a single deposited ovine B-cell or a pool of ovine B-cells together with/in the presence of phorbol myristate acetate (PMA).

One aspect as reported herein is the use of phorbol myristate acetate (PMA) in a cultivation of an ovine B-cell for improving cell growth.

One aspect as reported herein is a method for improving cell growth of ovine B-cells comprising the step of cultivating a single deposited ovine B-cell or a pool of ovine B-cells together with/in the presence of phorbol myristate acetate (PMA).

Methods and techniques known to a person skilled in the art, which are useful for carrying out the current invention, are described e.g. in Ausubel, F. M., ed., Current Protocols in Molecular Biology, Volumes I to III (1997), Wiley and Sons; Sambrook, et al., Molecular Cloning: A Laboratory Manual, Second Edition, Cold Spring Harbor Laboratory Press, Cold Spring Harbor, N.Y. (1989).

Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "amino acid" as used within this application denotes the group of carboxy α-amino acids, which directly or in form of a precursor can be encoded by a nucleic acid. The individual amino acids are encoded by nucleic acids consisting of three nucleotides, so called codons or base-triplets. Each amino acid is encoded by at least one codon. The encoding of the same amino acid by different codons is known as "degeneration of the genetic code". The term "amino acid" as used within this application denotes the naturally occurring carboxy α-amino acids and is comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The term "ovine-non-ovine species chimeric antibody" denotes an antibody comprising the variable domain of a parent ovine antibody and the constant region from an antibody of a different species, such as e.g. from a human antibody, a murine antibody, or a rabbit antibody. The term "ovine-non-ovine species chimeric antibody" denotes an antibody comprising the variable region of a parent ovine antibody and the constant region of a different species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "clone" denotes a population of dividing and antibody secreting B-cells arising from/originating from a single B-cell. Thus, a B-cell clone produces a monoclonal antibody.

The term "expression" as used herein refers to transcription and/or translation processes occurring within a cell. The level of transcription of a nucleic acid sequence of interest in a cell can be determined on the basis of the amount of corresponding mRNA that is present in the cell. For example, mRNA transcribed from a sequence of interest can be quantitated by RT-PCR or by Northern hybridization (see Sambrook, et al., 1989, supra). Polypeptides encoded by a nucleic acid of interest can be quantitated by various methods, e.g. by ELISA, by assaying for the biological activity of the polypeptide, or by employing assays that are independent of such activity, such as Western blotting or radioimmunoassay, using immunoglobulins that recognize and bind to the polypeptide (see Sambrook, et al., 1989, supra).

An "expression cassette" refers to a construct that contains the necessary regulatory elements, such as promoter and polyadenylation site, for expression of at least the contained nucleic acid in a cell.

Expression of a gene is performed either as transient or as permanent expression. The polypeptide(s) of interest are in general secreted polypeptides and therefore contain an N-terminal extension (also known as the signal sequence) which is necessary for the transport/secretion of the polypeptide through the cell wall into the extracellular medium.

In general, the signal sequence can be derived from any gene encoding a secreted polypeptide. If a heterologous signal sequence is used, it preferably is one that is recognized and processed (i.e. cleaved by a signal peptidase) by the host cell. For secretion in yeast for example the native signal sequence of a heterologous gene to be expressed may be substituted by a homologous yeast signal sequence derived from a secreted gene, such as the yeast invertase signal sequence, alpha-factor leader (including Saccharomyces, Kluyveromyces, Pichia, and Hansenula α-factor leaders, the second described in U.S. Pat. No. 5,010,182), acid phosphatase signal sequence, or the C. albicans glucoamylase signal sequence (EP 0 362 179). In mammalian cell expression the native signal sequence of the protein of interest is satisfactory, although other mammalian signal sequences may be suitable, such as signal sequences from secreted polypeptides of the same or related species, e.g. for immunoglobulins from human or murine origin, as well as viral secretory signal sequences, for example, the herpes simplex glycoprotein D signal sequence. The DNA fragment encoding for such a pre-segment is ligated in frame, i.e. operably linked, to the DNA fragment encoding a polypeptide of interest.

The term "experimental animal" denotes a non-human animal. In one embodiment the experimental animal is selected from rat, mouse, hamster, rabbit, camel, llama, non-human primates, sheep, dog, cow, chicken, amphibians, sharks and reptiles. In one embodiment the experimental animal is a sheep.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A., et al., Sequences of Proteins of Immunological Interest, 5th ed., Public Health Service, National Institutes of Health, Bethesda, Md. (1991), NIH Publication 91-3242, Vols. 1-3.

The term "feeder mix" denotes a combination of different additives, such as growth factors, cytokines and/or further proteins promoting the activation and/or survival of B-cells and/or antibody secretion. The feeder mix can be a natural feeder mix, e.g. obtained from the cultivation supernatant of thymocytes (TSN), which is a non-defined combination of cytokines, or the feeder mix can be a synthetic feeder mix, e.g. comprising a mixture of IL-21 and/or IL-2 and/or IL-6.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "cell" or "host cell" refers to a cell into which a nucleic acid, e.g. encoding a heterologous polypeptide, can be or is transfected. The term "cell" includes both prokaryotic cells, which are used for propagation of plasmids, and eukaryotic cells, which are used for the expression of a nucleic acid and production of the encoded polypeptide. In one embodiment, the eukaryotic cells are mammalian cells. In one embodiment the mammalian cell is a CHO cell or a HEK cell. In one embodiment the CHO cell is a CHO K1 cell (ATCC CCL-61 or DSM ACC 110), or a CHO DG44 cell (also known as CHO-DHFR[−], DSM ACC 126), or a CHO XL99 cell, a CHO-T cell (see e.g. Morgan, D., et al., Biochemistry 26 (1987) 2959-2963), or a CHO—S cell, or a Super-CHO cell (Pak, S. C. O., et al. Cytotechnol. 22 (1996) 139-146). In one embodiment the HEK cell is a HEK293 cell. If these cells are not adapted to growth in serum-free medium or in suspension an adaptation prior to the use in the current method is to be performed. As used herein, the expression "cell" includes the subject cell and its progeny. Thus, the words "transformant" and "transformed cell" include the primary subject cell and cultures derived there from without regard for the number of transfers or sub-cultivations. It is also understood that all progeny may not be precisely identical in DNA content, due to deliberate or inadvertent mutations. Variant progeny that have the same function or biological activity as screened for in the originally transformed cell are included.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A., et al., Sequences of Proteins of Immunological Interest, 5th ed., Public Health Service, National Institutes of Health, Bethesda, Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs herein include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

The term "labeling" denotes the presence or absence of a surface marker which can be determined by the addition of a specifically binding and labeled anti-surface marker antibody. Thus, the presence of a surface marker is determined e.g. in the case of a fluorescence label by the occurrence of a fluorescence whereas the absence of a surface marker is determined by the absence of a fluorescence after incubation with the respective specifically binding and labeled anti-surface marker antibody.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

A "nucleic acid" or a "nucleic acid sequence", which terms are used interchangeably within this application, refers to a polymeric molecule consisting of individual nucleotides (also called bases) a, c, g, and t (or u in RNA), for example to DNA, RNA, or modifications thereof. This polynucleotide molecule can be a naturally occurring polynucleotide molecule or a synthetic polynucleotide molecule or a combination of one or more naturally occurring polynucleotide molecules with one or more synthetic polynucleotide molecules. Also encompassed by this definition are naturally occurring polynucleotide molecules in which one or more nucleotides are changed (e.g. by mutagenesis), deleted, or added. A nucleic acid can either be isolated, or integrated in another nucleic acid, e.g. in an expression cassette, a plasmid, or the chromosome of a host cell. A nucleic acid is characterized by its nucleic acid sequence consisting of individual nucleotides.

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

The term "specifically binding" and grammatical equivalents thereof denote that the antibody binds to its target with a dissociation constant (Kd) of $10^{-7}$M or less, in one embodiment of from $10^{-8}$M to $10^{-13}$M, in a further embodiment of from $10^{-9}$M to $10^{-13}$ M. The term is further used to indicate that the antibody does not specifically bind to other biomolecules present, i.e. it binds to other biomolecules with a dissociation constant (Kd) of $10^{-6}$ M or more, in one embodiment of from $10^{-6}$M to 1 M.

A "transfection vector" is a nucleic acid (also denoted as nucleic acid molecule) providing all required elements for the expression of the in the transfection vector comprised coding nucleic acids/structural gene(s) in a host cell. A transfection vector comprises a prokaryotic plasmid propagation unit, e.g. for E. coli, in turn comprising a prokaryotic origin of replication, and a nucleic acid conferring resistance to a prokaryotic selection agent, further comprises the transfection vector one or more nucleic acid(s) conferring resistance to an eukaryotic selection agent, and one or more nucleic acid encoding a polypeptide of interest. Preferably are the nucleic acids conferring resistance to a selection agent and the nucleic acid(s) encoding a polypeptide of interest placed each within an expression cassette, whereby each expression cassette comprises a promoter, a coding nucleic acid, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J., et al., Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S., et al., J. Immunol. 150 (1993) 880-887; Clackson, T., et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "young animal" denotes an animal before sexual maturity occurs. A young hamster, for example, is of an age of less than 6 weeks, especially less than 4 weeks. A young mouse, for example, is of an age of less than 8 weeks, especially less than 5 weeks.

Immunization

In the methods as reported herein B-cells obtained from sheep are used/processed.

In one embodiment the B-cell is an ovine B-cell. In one embodiment the ovine B-cell is obtained from an immunized sheep or from a sheep after vaccination against a specific antigen.

Source and Isolation of B-Cells

The blood of an immunized experimental animal provides a high diversity of antibody producing B-cells. The therefrom obtained B-cells generally secrete antibodies that have almost no identical or overlapping amino acid sequences within the CDRs and, thus, show a high diversity.

In one embodiment the B-cells of an experimental animal, e.g. obtained from the blood of the experimental animal are obtained of from 4 days after immunization until 15 days after immunization or the most recent boost.

In one embodiment the B-cells are obtained after of from 4 days until at most 9 days after immunization or the most recent boost.

This time span allows for a high flexibility in the method as reported herein. In this time span it is likely that the B-cells providing for the most affine antibodies migrate from spleen to blood (see e.g. Paus, D., et al., JEM 203 (2006) 1081-1091; Smith, K. G. S., et al., The EMBO J. 16 (1997) 2996-3006; Wrammert, J., et al., Nature 453 (2008) 667-672).

Selection Steps Prior to Co-Cultivation

B-cells producing antibodies that specifically bind an antigen can be enriched from peripheral blood mononuclear cells (PBMCs). Thus, in one embodiment of all methods as reported herein the B-cell is obtained from peripheral blood mononuclear cells (PBMCs) or the pool of B-cells is enriched from peripheral blood mononuclear cells (PBMCs).

Cells not producing an antibody binding the antigen of interest or, likewise, cells producing an antibody binding to the antigen of interest can be reduced or enriched, respectively, by using a panning approach. Therein a binding partner is presented attached to a surface and cells binding thereto are selectively enriched in the cell population in case the bound cells are processed further or reduced in the cell population in case the cells remaining in solution are processed further.

The method as reported herein comprises in one embodiment a selecting step in which B-cells producing specific antibodies are selected based on cell surface markers and fluorescence activated cell sorting/gating. In one embodiment mature B-cells are sorted/enriched/selected. For selection of B-cells from different experimental animal species different cell surface markers can be used.

With the labeling of non-target cell populations and non-specifically binding lymphocytes it is possible to selectively deplete these cells. In this depletion step generally a non-total depletion can be achieved. Albeit the depletion is not quantitative it provides for an advantage in the succeeding fluorescence labeling of the remaining cells as the number of interfering cells can be reduced or even minimized.

Different cell populations can be labeled by using different surface markers such as $CD3^+$-cells (T-cells), $CD19^+$-cells (B-cells in general), $IgM^+$-cells (mature naive B-cells), $IgG^+$-cells (mature B-cells), $CD38^+$-cells (e.g. plasmablasts), and $IgG^+CD38^+$-cells (pre-plasma cells).

In one embodiment ovine B-cell(s) is/are labeled/selected that are IgG positive and CD45R positive ($IgG^+CD45R^+$).

In one embodiment ovine B-cell(s) is/are labeled/selected that are IgG positive and CD21 positive ($IgG^+CD21^+$).

An immuno-fluorescence labeling for selection of mature $IgG^+$-B-cells, such as memory B-cells, plasmablasts, and plasma cells can be used in the methods as reported herein.

For a selection or enrichment of B-cells the cells are either single labeled, or double labeled, or triple labeled.

Single Cell Depositing

The methods as reported herein in one embodiment comprise the step of depositing the B-cells of a B-cell population as single cells.

In one embodiment the depositing as single cells is by fluorescence activated cell sorting (FACS).

In one embodiment specifically labeled B-cells are deposited as single cells. In one embodiment the labeling is a labeling of cell surface markers with fluorescence labeled antibodies.

In one embodiment the methods as reported herein provide for monoclonal antibodies.

In one embodiment of all methods as reported herein the B-cell is a mature B-cell and mature B-cells are deposited as single cells.

The immuno fluorescence labeling used for B-cells obtained from the blood of an experimental animal can also be used for the labeling of B-cells obtained from the spleen and other immunological organs of an experimental animal.

Multi Cell Depositing

The methods as reported herein in one embodiment comprise the step of depositing a pool of B-cells. In this pool of B-cells a total number of B-cells are deposited per well after magnetic affinity bead or FACS isolation from peripheral blood.

In one embodiment about 50 B-cells are deposited.

In one embodiment about 500 B-cells are deposited.

In one embodiment about 2,500 B-cells are deposited.

The total number of deposited B-cells can, e.g. for ovine B-cells, be increased up to 90,000 B-cells or more in a single experiment.

Cultivation

Herein is reported the cultivation of antibody producing B-cells together with/in the presence of phorbol myristate acetate (PMA).

Thus, in one embodiment of all methods as reported herein the B-cells, either as pool of B-cells or as single deposited B-cells, are cultivated together with/in the presence of phorbol myristate acetate (PMA) and feeder cells.

Already after about 3, 4, 5, 6, 7, 8, 10, 15, or 21 days of cultivation a sufficient amount/number of antibody molecules is obtained in the supernatant. With the therewith provided amount of antibody different analyses can be performed in order to characterize the antibody, e.g. regarding binding specificity, in more detail. With the improved characterization of the antibody at this early stage in the screening/selection process it is possible to reduce the number of required nucleic acid isolations and sequencing reactions that have to be performed.

In one embodiment the cultivation time is about 5 to 10 days. In one specific embodiment the cultivation time is about 7 days.

In one embodiment of all methods as reported herein is the cultivation of antibody producing B-cells in the presence of phorbol myristate acetate (PMA), feeder cells and a feeder mix.

The feeder mix can be a natural feeder mix or a synthetic feeder mix.

A natural feeder mix is e.g. thymocyte supernatant (TSN). It contains appropriate soluble factors, but this reagent is heterogeneous, the ingredients are not adequately described and differ from animal to animal.

In one embodiment of all methods as reported herein the feeder mix is an ovine thymocyte cultivation supernatant. In one embodiment the B-cell is an ovine B-cell.

In one embodiment the thymocyte cultivation supernatant is obtained from the cultivation of thymocytes of the thymus gland of the respective young animal. It is especially suited to use the thymus gland of young animals compared to the isolation of thymocytes from the blood of adult animals.

In general the cultivation step of ovine B-cells together with/in the presence of phorbol myristate acetate (PMA) in the methods as reported herein can be preceded and also succeeded by a number of additional steps.

In one embodiment of all methods as reported herein the co-cultivation of antibody producing B-cells and feeder cells is in the presence of ovine thymocyte supernatant (ovine TSN), and/or phorbol myristate acetate (PMA), and/or formalin-fixed *Staphylococcus* A strain Cowan 1 particles (SAC). In one embodiment the B-cell is an ovine B-cell and the feeder cell is a murine EL4B5 cells. In one embodiment PMA and SAC are added at the start of the cultivation together with the cultivation medium.

In one embodiment of all methods as reported herein the cultivation of antibody producing ovine B-cells and feeder cells is in the presence of PMA and SAC, whereby PMA and SAC are added at the start of the cultivation together with the cultivation medium.

It has been found that the use of a cultivation system comprising a B-cell and PMA results in an improved proliferation of the B-cell, i.e. the B-cell divides more rapidly and higher cell densities and antibody titer in the cultivation supernatant, respectively, can be obtained in shorter time compared to a system not comprising PMA.

It has further been found that for ovine B-cells a co-cultivation system comprising PMA, ovine TSN and SAC is especially suited.

Characterization of Co-Cultivated Cells by IgG Production

For the (qualitative and quantitative) determination of secreted IgG after the co-cultivation generally all methods known to a person of skill in the art such as an ELISA can be used. In one embodiment of all methods as reported herein an ELISA is used.

Depending on the characterization results a B-cell clone can be obtained, i.e. selected.

Characterization of Co-Cultivated Cells by Expansion and Proliferation

For the (qualitative and quantitative) determination of cellular expansion the proliferation or viability of the co-cultivated B-cells can be assessed using different readout systems (commercial cellular activity test "cell titer glow" (Promega), the CFSE dilution method, $^3H$Thymidin incorporation, or cell culture images).

Isolation of mRNA, Cloning and Sequencing

A B-cell clone producing high antibody titers provides an amount of mRNA encoding (cognate) monoclonal light and heavy chain variable region allowing the use of degenerated PCR primer and obviates the requirement of highly specific PCR primer. Also the required number of PCR cycles is reduced. Thus, in one embodiment the reverse transcriptase PCR is with degenerated PCR primer for the light and heavy chain variable domain.

From the B-cells the total mRNA can be isolated and transcribed in cDNA. With the respective primer the cognate VH- and VL-region encoding nucleic acid can be amplified.

In one embodiment of all methods as reported herein the amino acid sequence is derived from the amplified variable domain-encoding nucleic acid. The exact start and end point of the variable domain-encoding nucleic acid is identified by locating the amino acid sequences for example of QVQL/QVRL to VSS/VSK (VH-region), for example QAVLT to VLGQP (VL lambda-region), and for example DVVL/DIQV to VEIKRSD (VL kappa region).

Pool Analysis

To exemplify the current invention PBMCs were isolated from sheep immunized with a KLH-conjugated hapten and underwent positive panning using the biotinylated hapten and magnetic streptavidin beads to enrich antigen-specific B-cells. Subsequently, B-cells were stained for both surface IgG (sIgG) and the B-cell marker CD45R or CD21. Pools of 50 cells (sIgG$^+$CD45R$^+$ or sIgG$^+$CD21$^+$) were sorted into 96-well plates using a BD FACS Aria cell sorter. Cells were cultivated in medium supplemented with different factors in order to identify a medium composition that promotes the proliferation of the B-cells as well as the differentiation to IgG secreting cells (i.e. plasma cells)

In all experiment the basal medium was supplemented with 10% FCS, SAC and sheep TSN. Cells were cultivated in the presence of EL4B5 feeder cells.

IgG Secretion by In Vitro Cultivated sIgG$^+$CD45R$^+$ B-Cells

Pools of 50 cells/well of antigen-enriched sIgG$^+$CD45R$^+$ B-cells were cultivated in the different media in a 96-well plate in the presence of EL4B5 feeder cells. After one week of cultivation the sheep IgG concentration of the supernatants was analyzed using a sheep IgG ELISA. The results for IMDM as basal medium are presented in FIG. 1 and for DMEM and IMDM as basal medium in the following Table.

TABLE

| cultivation medium | relative % of IgG positive wells with an IgG concentration of 50-400 ng/ml |
|---|---|
| IMDM | 18 |
| IMDM + IL-6 | 68 |
| IMDM + IL-4 | 73 |
| IMDM + IL-6 + IL-4 | 86 |
| IMDM + LPS | 68 |
| IMDM + PMA | 100 |
| DMEM | 5 |
| DMEM + IL-6 | 5 |
| DMEM + IL-4 | 27 |
| DMEM + IL-6 + IL-4 | 36 |
| DMEM + LPS | 27 |
| DMEM + PMA | 64 |

IMDM = Iscove's Modified Dulbecco's Medium
IL-6 = human interleukin 6
IL-4 = human interleukin 4
LPS = Lipopolysaccharide
PMA = phorbol myristate acetate
DMEM—Dulbecco's Modified Eagle's Medium It can be seen that the basal medium itself (DMEM or IMDM supplemented with 10% FCS, SAC and sheep TSN) does not efficiently promote the proliferation/differentiation of sheep B-cells since only 5% or 18%, respectively, of the wells contained significant concentrations of sheep IgG (>50 ng/ml). An increase of the number of IgG-containing wells was noticed when the basal medium was supplemented with IL-4 and/or IL-6 or LPS. Surprisingly when PMA was added to the basal medium 64% or 100%, respectively, of the wells were found to contain significant concentrations of IgG (>50 ng/ml).

For a more detailed analysis 4 categories of wells were defined: Wells with no IgG producing cells (IgG concentration below limit of detection, i.e. <10 ng/ml), wells with low IgG concentrations (10-50 ng/ml), wells with an average IgG concentration (50-200 ng/ml) and wells with a high IgG concentration (200-400 ng/ml). The results are presented in following Tables.

TABLE

| cultivation medium | number of IgG positive wells with an IgG concentration of | | | |
|---|---|---|---|---|
| | 0-10 ng/ml | 10-50 ng/ml | 50-200 ng/ml | 200-400 ng/ml |
| IMDM | 5 | 13 | 3 | 1 |
| IMDM + IL-6 | 0 | 7 | 14 | 1 |
| IMDM + IL-4 | 1 | 5 | 15 | 1 |
| IMDM + IL-6 + IL-4 | 1 | 2 | 16 | 2 |
| IMDM + LPS | 5 | 2 | 15 | 0 |
| IMDM + PMA | 0 | 0 | 22 | 0 |
| DMEM | 8 | 13 | 1 | 0 |
| DMEM + IL-6 | 9 | 12 | 1 | 0 |
| DMEM + IL-4 | 12 | 4 | 6 | 0 |
| DMEM + IL-6 + IL-4 | 5 | 9 | 8 | 0 |
| DMEM + LPS | 2 | 14 | 6 | 0 |
| DMEM + PMA | 1 | 7 | 14 | 0 |

TABLE

| cultivation medium | relative % of IgG positive wells with an IgG concentration of | | | |
|---|---|---|---|---|
| | 0-10 ng/ml | 10-50 ng/ml | 50-200 ng/ml | 200-400 ng/ml |
| IMDM | 22.7 | 59.1 | 13.6 | 4.6 |
| IMDM + IL-6 | 0 | 31.8 | 63.6 | 4.6 |
| IMDM + IL-4 | 4.6 | 22.7 | 68.2 | 4.6 |
| IMDM + IL-6 + IL-4 | 4.8 | 9.5 | 76.2 | 9.5 |
| IMDM + LPS | 22.7 | 9.1 | 68.2 | 0 |
| IMDM + PMA | 0 | 0 | 100 | 0 |
| DMEM | 36.4 | 59.1 | 4.6 | 0 |
| DMEM + IL-6 | 40.9 | 54.6 | 4.6 | 0 |
| DMEM + IL-4 | 54.6 | 18.2 | 27.3 | 0 |
| DMEM + IL-6 + IL-4 | 22.7 | 40.9 | 36.4 | 0 |
| DMEM + LPS | 9.1 | 63.6 | 27.3 | 0 |
| DMEM + PMA | 4.6 | 31.8 | 63.6 | 0 |

IMDM = Iscove's Modified Dulbecco's Medium
IL-6 = human interleukin 6
IL-4 = human interleukin 4
LPS = Lipopolysaccharide
PMA = phorbol myristate acetate
DMEM—Dulbecco's Modified Eagle's Medium It can be seen that e.g. for IMDM as basal medium supplementation of medium with IL-6 and/or IL-4 has a comparable effect resulting in approx. 60-70% of wells with an average IgG concentration and a few numbers of wells with a high IgG concentration (approx. 5-9% of wells). Similar results were obtained for LPS stimulation of cells. Stimulation with PMA results in 100% of wells with an average IgG concentration in the range of 50-200 ng/ml.

IgG Secretion by In Vitro Cultivated sIgG$^+$CD21$^+$ B-Cells

Figure 2:
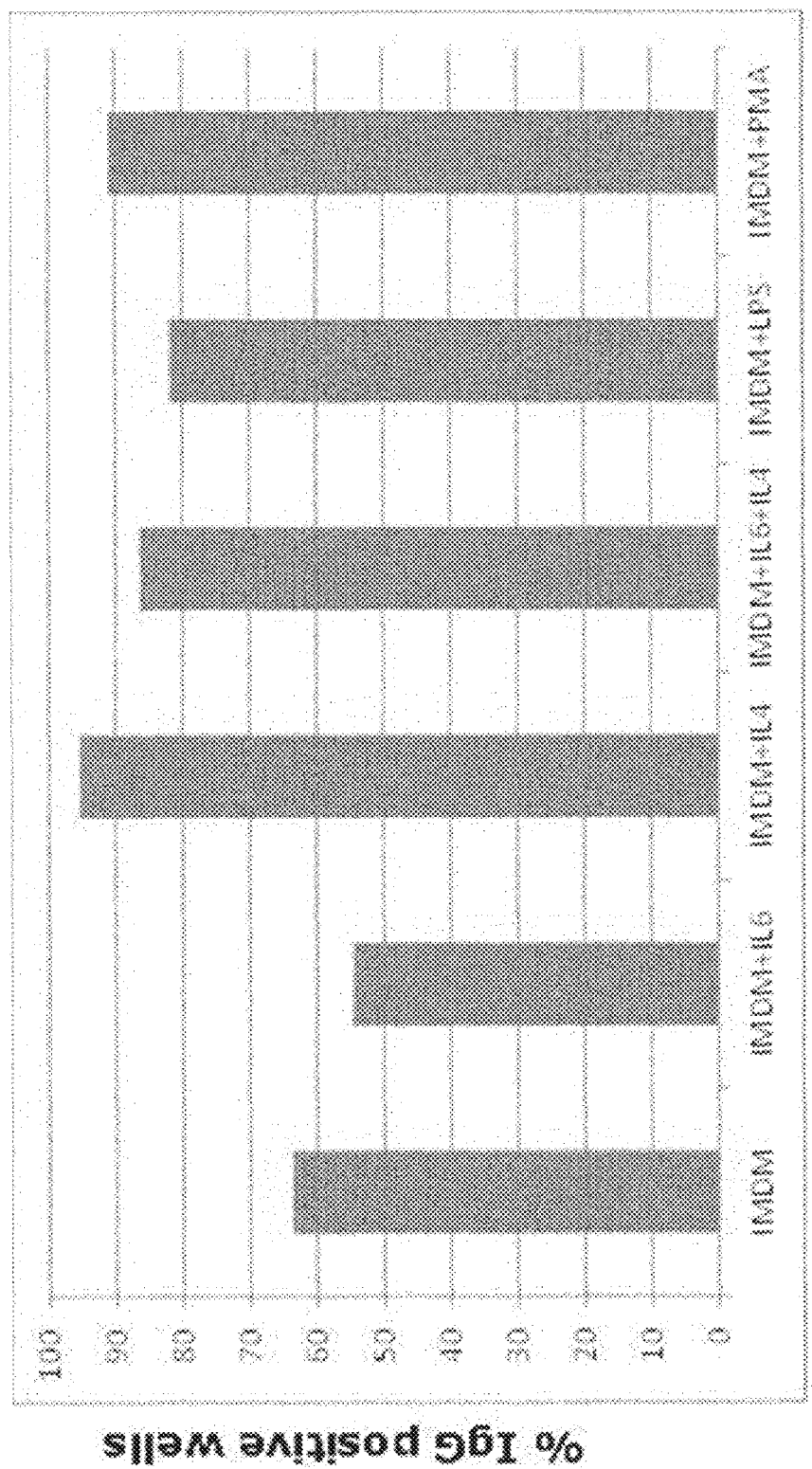
FIG. 2 IgG secretion by in vitro cultivated sIgG$^+$CD21$^+$ B-cells.

Pools of 50 cells/well of antigen-enriched sIgG$^+$CD21$^+$ B-cells were cultivated in the indicated medium in a 96-well plate in the presence of EL4B5 feeder cells. After one week of cultivation the sheep IgG concentration of the supernatants was analyzed using a sheep IgG ELISA. The results for IMDM as basal medium are presented in FIG. 2 and for DMEM and IMDM as basal medium in the following Table.

TABLE

| cultivation medium | relative % of IgG positive wells with an IgG concentration of 50-400 ng/ml |
|---|---|
| IMDM | 64 |
| IMDM + IL-6 | 57 |
| IMDM + IL-4 | 95 |
| IMDM + IL-6 + IL-4 | 86 |
| IMDM + LPS | 82 |
| IMDM + PMA | 91 |
| DMEM | 45 |
| DMEM + IL-6 | 0 |
| DMEM + IL-4 | 0 |
| DMEM + IL-6 + IL-4 | 0 |
| DMEM + LPS | 100 |
| DMEM + PMA | 91 |

IMDM = Iscove's Modified Dulbecco's Medium
IL-6 = human interleukin 6
IL-4 = human interleukin 4
LPS = Lipopolysaccharide
PMA = phorbol myristate acetate
DMEM—Dulbecco's Modified Eagle's Medium It can be seen that the basal medium (DMEM or IMDM supplemented with 10% FCS, SAC and sheep TSN) promotes the proliferation/differentiation of sIgG+CD21+ sheep B-cells. For IMDM as basal medium approx. 60% of the wells contained significant concentrations of sheep IgG (>50 ng/ml). An increase of the number of IgG-containing wells was noticed when the basal medium was supplemented with IL-4 or LPS Likewise, addition of PMA to the basal medium increased the number of wells containing significant levels of IgG (approx. 90%).

For a more detailed analysis 4 categories of wells were defined: Wells with no IgG producing cells (IgG concentration below limit of detection, i.e. <10 ng/ml), wells with low IgG concentrations (10-50 ng/ml), wells with an average IgG concentration (50-200 ng/ml) and wells with a high IgG concentration (200-400 ng/ml). The results are presented in following Tables.

TABLE

| cultivation medium | number of IgG positive wells with an IgG concentration of | | | |
|---|---|---|---|---|
| | 0-10 ng/ml | 10-50 ng/ml | 50-200 ng/ml | 200-400 ng/ml |
| IMDM | 0 | 8 | 14 | 0 |
| IMDM + IL-6 | 1 | 9 | 12 | 1 |
| IMDM + IL-4 | 0 | 1 | 20 | 1 |
| IMDM + IL-6 + IL-4 | 2 | 1 | 16 | 3 |
| IMDM + LPS | 0 | 4 | 16 | 2 |
| IMDM + PMA | 0 | 2 | 9 | 11 |
| DMEM | 10 | 2 | 10 | 0 |
| DMEM + IL-6 | 22 | 0 | 0 | 0 |

TABLE-continued

| cultivation medium | number of IgG positive wells with an IgG concentration of | | | |
|---|---|---|---|---|
| | 0-10 ng/ml | 10-50 ng/ml | 50-200 ng/ml | 200-400 ng/ml |
| DMEM + IL-4 | 22 | 0 | 0 | 0 |
| DMEM + IL-6 + IL-4 | 22 | 0 | 0 | 0 |
| DMEM + LPS | 0 | 0 | 11 | 11 |
| DMEM + PMA | 1 | 1 | 17 | 3 |

TABLE

| cultivation medium | relative % of IgG positive wells with an IgG concentration of | | | |
|---|---|---|---|---|
| | 0-10 ng/ml | 10-50 ng/ml | 50-200 ng/ml | 200-400 ng/ml |
| IMDM | 0 | 36.4 | 63.6 | 0 |
| IMDM + IL-6 | 4.3 | 39.1 | 52.2 | 4.3 |
| IMDM + IL-4 | 0 | 4.6 | 90.9 | 4.6 |
| IMDM + IL-6 + IL-4 | 9.1 | 4.6 | 72.7 | 13.6 |
| IMDM + LPS | 0 | 18.2 | 72.7 | 9.1 |
| IMDM + PMA | 0 | 9.1 | 40.9 | 50.0 |
| DMEM | 45.5 | 9.1 | 45.5 | 0 |
| DMEM + IL-6 | 100 | 0 | 0 | 0 |
| DMEM + IL-4 | 100 | 0 | 0 | 0 |
| DMEM + IL-6 + IL-4 | 100 | 0 | 0 | 0 |
| DMEM + LPS | 0 | 0 | 50.0 | 50.0 |
| DMEM + PMA | 4.6 | 4.6 | 77.3 | 13.6 |

IMDM = Iscove's Modified Dulbecco's Medium
IL-6 = human interleukin 6
IL-4 = human interleukin 4
LPS = Lipopolysaccharide
PMA = phorbol myristate acetate
DMEM—Dulbecco's Modified Eagle's Medium It can be seen that e.g. for IMDM as basal medium the supplementation of medium with IL-4 or LPS has a comparable effect resulting in approx. 70-90% of wells with an average IgG concentration and a few numbers of wells with a high IgG concentration (approx. 5-10% of wells). In contrast, stimulation with PMA leads to approx. 50% of wells with a high IgG concentration and approx. 40% with an average IgG concentration.

Single Cell Analysis

Sorting and Cultivation of Single sIgG+CD21+ B-Cells

PBMCs were isolated from sheep immunized with a KLH-conjugated hapten, underwent positive panning for enrichment of antigen-specific B-cells and were stained for both sheep sIgG and CD21. Single cells were sorted in 96-well plates using a BD FACS Aria cell sorter. Cells were cultivated in IMDM supplemented with 10% FCS, SAC, sheep TSN and PMA. Cells were cultivated in the presence of EL4B5 feeder cells. After one week of cultivation, the IgG concentration of the supernatant of the cells was analyzed by ELISA. The results are shown in FIG. 3.

Figure 3:
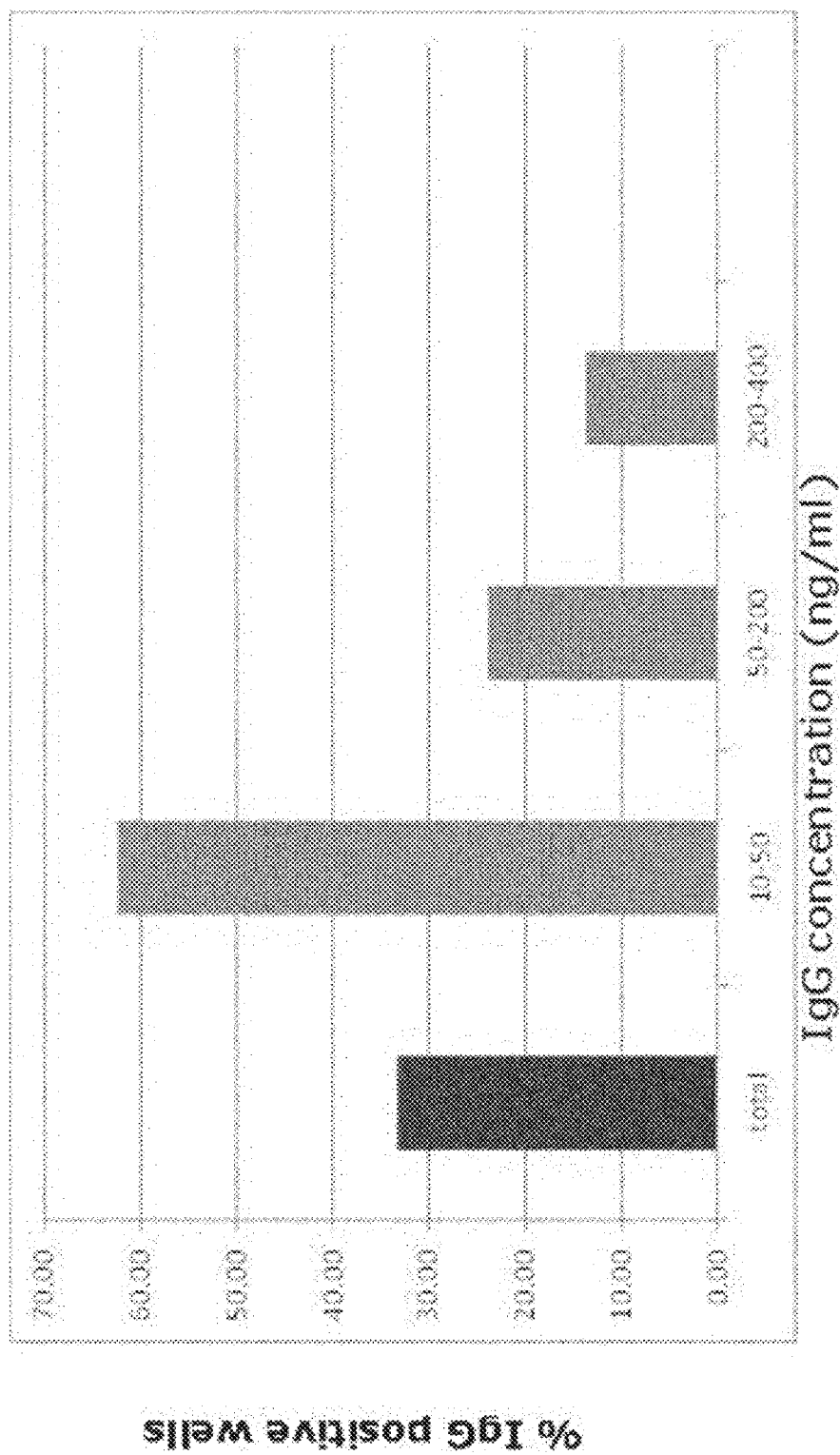
FIG. 3 Sorting and cultivation of single deposited sIgG$^+$ CD21$^+$ B-cells; most left column: overall IgG positive wells; middle column and right columns: relative percentage of the total percentage with specific productivity.

After one week of cultivation a total of 33% wells contained IgG-secreting B-cell clones (left column in FIG. 3). In turn, 62% of these wells with IgG-secreting clones contained a low IgG concentration (10-50 ng/ml, $2^{nd}$ to left column in FIG. 3), 24% contained an average IgG concentration (50-200 ng/ml, $2^{nd}$ to right column in FIG. 3) and 14% contained a high IgG concentration (200-400 ng/ml, right column in FIG. 3).

The specificity of the secreted antibodies was analyzed using an antigen-specific ELISA (data not shown). These ELISAs demonstrate that 38% of the total IgG-secreting clones produced antibodies that are antigen-specific.

This experiment was performed again. PBMCs were isolated from sheep immunized with another KLH-conjugated hapten, underwent positive panning for enrichment of antigen-specific B-cells and were stained for both sheep sIgG and CD21. Double-positive single cells were sorted in 96-well plates using a BD FACS Aria cell sorter. Cells were cultivated in IMDM supplemented with 10% FCS, SAC, sheep TSN and PMA in the presence of EL4B5 feeder cells.

In control experiments single cells were cultivated using the same cultivation conditions in the absence of PMA. After one week of cultivation, the IgG concentration of the cell supernatants was analyzed by ELISA. After one week of cultivation in the presence of PMA a total of approx. 16% of total wells contained IgG-secreting B-cell clones. In turn, 35% of the wells with IgG-secreting clones contained a low IgG concentration, 35% contained an average IgG concentration and 30% contained a high IgG concentration. In the absence of PMA none of the wells contained IgG-secreting B-cell clones.

Additionally, the specificity of the secreted antibodies was analyzed using an antigen-specific ELISA (data not shown). These ELISAs demonstrate that 29% of the IgG-secreting clones produced antibodies that are antigen-specific.

The results of the experiment are summarized in the Tables below.

TABLES

| cultivation medium | No. IgG positive wells | % IgG positive wells | No. wells with antigen-specific IgG | % wells with antigen-specific IgG |
|---|---|---|---|---|
| with PMA | 66 | 15.7 | 19 | 28.8 |
| w/o PMA | 0 | 0 | 0 | 0 |

| cultivation medium | wells with low IgG conc. | wells with medium IgG conc. | wells with high IgG conc. |
|---|---|---|---|
| with PMA | 23 | 23 | 20 |
| w/o PMA | 0 | 0 | 0 |

| | wells with low IgG conc. | wells with medium IgG conc. | wells with high IgG conc. |
|---|---|---|---|
| with PMA | 34.8% | 34.8% | 30.3% |
| w/o PMA | 0 | 0 | 0 |

Specific Embodiments

1. A method for cultivating a B-cell, wherein the method comprises the following step:
   cultivating a B-cell in the presence of/together with phorbol myristate acetate (PMA).
2. A method for producing an ovine antibody, wherein the method comprises the following steps
   cultivating an antibody secreting B-cell in the presence of/together with phorbol myristate acetate (PMA), and
   recovering the antibody from the cultivation supernatant, thereby producing the antibody.
3. Use of phorbol myristate acetate (PMA) in the cultivation of an antibody secreting B-cell.
4. A method for improving cell growth of a B-cell, wherein the method comprises the following step
   cultivating a B-cell together with/in the presence of phorbol myristate acetate (PMA).
5. The method according to any one of embodiments 1 to 4, wherein the B-cell is an ovine B-cell.

6. The method according to any one of embodiments 1 to 5, wherein the B-cell is a single deposited B-cell or a pool of deposited B-cells.
7. The method according to embodiment 6, wherein the pool of deposited B-cells comprises of from about 10 B-cells to about 1,000,000 B-cells.
8. The method according to any one of embodiments 6 to 7, wherein the pool of deposited B-cells comprises of from about 25 B-cells to about 100,000 B-cells.
9. The method according to any one of embodiments 6 to 8, wherein the pool of deposited B-cells comprises about 50 B-cells.
10. The method according to any one of embodiments 1 to 9, wherein the cultivating is additionally in the presence of/together with feeder cells.
11. The method according to embodiment 10, wherein the feeder cells are EL4B5 cells.
12. The method according to any one of embodiments 1 to 11, wherein the cultivating is additionally in the presence of/together with thymocyte supernatant (TSN).
13. The method according to embodiment 12, wherein the TSN is ovine TSN.
14. The method according to any one of embodiments 1 to 13, wherein the cultivating is additionally in the presence of formalin-fixed *Staphylococcus* A strain Cowan 1 particles (SAC).
15. The method according to any one of embodiments 1 to 14, wherein the cultivating is in the presence of/together with phorbol myristate acetate (PMA), ovine TSN, SAC and feeder cells.
16. The method according to any one of embodiments 1 to 15, wherein the B-cell is an IgG positive B-cell (IgG$^+$).
17. The method according to any one of embodiments 1 to 16, wherein the B-cell is a naive or non-mature B-cell.
18. The method according to any one of embodiments 1 to 17, wherein the B-cell is an IgG positive and CD45R positive B-cell (IgG$^+$CD45R$^+$).
19. The method according to any one of embodiments 1 to 16, wherein the B-cell is a mature B-cell.
20. The method according to any one of embodiments 1 to 16 and 19, wherein the B-cell is an IgG positive and CD21 positive B-cell (IgG$^+$CD21$^+$).
21. The method according to any one of embodiments 1 to 20, wherein the method is for producing an antibody, which specifically binds to an antigen.
22. The method according to any one of embodiment 1 to 21, wherein the method comprises the following steps:
    a) cultivating a deposited antibody secreting B-cell in the presence/together with phorbol myristate acetate (PMA),
    b) isolating a nucleic acid encoding the amino acid sequence of the variable light chain domain and isolating a nucleic acid encoding the amino acid sequence of the variable heavy chain domain of an antibody, which specifically binds to an antigen,
    c) cultivating a cell comprising the nucleic acid isolated in b) or a variant thereof encoding a humanized version of the light and/or heavy chain variable domain within one or more expression cassettes,
    d) recovering the antibody from the cell or the cultivation medium and thereby producing an antibody, which specifically binds to an antigen.
23. The method according to any one of embodiment 1 to 22, wherein the method comprises the following steps:
    a) providing a population of antibody secreting B-cells,
    b) staining the cells of the population of B-cells with at least one fluorescence dye (in one embodiment with one to three, or two to three fluorescence dyes),
    c) depositing single cells of the stained population of B-cells or a pool of cells from the stained population of B-cells in individual containers (in one embodiment is the container a well of a multi well plate),
    d) cultivating the deposited individual B-cells in the presence of phorbol myristate acetate (PMA),
    e) determining the binding specificity of the antibodies secreted in the cultivation of the individual or pool of B-cells,
    f) determining the amino acid sequence of the variable light and heavy chain domain of specifically binding antibodies by a reverse transcriptase PCR and nucleotide sequencing, and thereby obtaining a monoclonal antibody variable light and heavy chain domain encoding nucleic acid,
    g) introducing the monoclonal antibody light and heavy chain variable domain encoding nucleic acid in an expression cassette for the expression of an antibody,
    h) introducing the nucleic acid in a cell,
    i) cultivating the cell and recovering the antibody from the cell or the cell culture supernatant and thereby producing an antibody, which specifically binds to an antigen.
24. The method according to any one of embodiments 1 to 23, wherein the method comprises the following steps:
    a) providing a population of antibody secreting B-cells,
    b) staining the cells of the population of B-cells with at least one fluorescence dye (in one embodiment with one to three, or two to three fluorescence dyes),
    c) depositing single cells of the stained population of B-cells or a pool of cells from the stained population of B-cells in individual containers (in one embodiment is the container a well of a multi well plate),
    d) cultivating the deposited ovine B-cells in the presence of phorbol myristate acetate (PMA),
    e) determining the binding specificity of the antibodies secreted in the cultivation of the ovine B-cells,
    f) determining the amino acid sequence of the variable light and heavy chain domain of specifically binding antibodies by a reverse transcriptase PCR and nucleotide sequencing, and thereby obtaining a monoclonal antibody variable light and heavy chain domain encoding nucleic acid,
    g) introducing the monoclonal antibody light and heavy chain variable domain encoding nucleic acid in an expression cassette for the expression of an antibody,
    h) introducing the nucleic acid in a cell,
    i) cultivating the cell and recovering the antibody from the cell or the cell culture supernatant and thereby producing an antibody, which specifically binds to an antigen.
25. The method according to any one of embodiments 2 and 5 to 24, wherein the antibody is a humanized antibody.
26. The method according to any one of embodiments 2 and 5 to 24, wherein the antibody is a chimeric antibody.
27. The method according to embodiment 26, wherein the chimeric antibody is an ovine-murine chimeric antibody or an ovine-rabbit chimeric antibody or an ovine-human chimeric antibody.
28. An antibody obtained with a method according to any one of embodiments 1 to 27.

The following examples, figures and sequences are provided to aid the understanding of the present invention, the true scope of which is set forth in the appended claims. It is understood that modifications can be made in the procedures set forth without departing from the spirit of the invention.

Examples

Material & Methods
Preparation of Ovine TSN (Thymocyte Supernatant)
Preparation of Ovine Thymocytes:

The thymus was removed from a Suffolk-Merino sheep, cut into pieces and mashed through a cell strainer. Cells of the thymus were collected in RPMI medium (Gibco, Paisley, UK) supplemented with 10% FCS (Hyclone, Logan, Utah, USA), L-Penicillin-Streptomycin-Glutamine (1×) (Gibco), 10 mM HEPES (Gibco), 2 mM Sodium pyruvate (Gibco) and 55 µM 2-Mercaptoethanol (Gibco). Cells were centrifuged at 800×g for 10 min. and resuspended in the medium. After counting of viable cells the cell suspension was centrifuged again and the cell pellet was resuspended in freezing medium (RPMI medium containing 20% FCS and 10% DMSO) at $1\times10^8$ cells/ml. Aliquots of the cells were frozen using a cell freezing container (Nalgene Mr. Frosty, Thermo Fisher Scientific) filled with isopropyl alcohol at −80° C. and subsequently stored in liquid nitrogen.
Preparation of Ovine Macrophages:

Approx. 50 ml of EDTA-blood was taken from a Suffolk-Merino sheep and mixed with an equal volume of PBS (phosphate buffered saline). Aliquots of 15 ml of the diluted blood were layered on 12.5 ml Lympholyte®-Mammal (Cedarlane, Ontario, Canada) and centrifuged for 30 min. at 800×g. After centrifugation the PBMCs (peripheral blood mononuclear cells) were collected, washed with PBS and counted using a counting chamber. The cells were seeded into a T175 cell culture flask (Greiner Bio-One, Frickenhausen, Germany) at $1\times10^6$ cells/ml in RPMI medium (Gibco) supplemented with 10% FCS (Hyclone), L-Penicillin-Streptomycin-Glutamine (1×) (Gibco), 10 mM HEPES (Gibco), 2 mM Sodium pyruvate (Gibco) and 55 µM 2-Mercaptoethanol (Gibco). Cells were incubated at 37° C./5% $CO_2$ in a humidified atmosphere for 48 hours. Subsequently non-adherent cells were removed by gently washing of the cells with medium, while the adherent cells (macrophage enriched population) were used for preparation of TSN by co-cultivation with thymocytes as described below.
Co-Cultivation of Ovine Thymocytes and Macrophages Frozen thymocytes were thawed and seeded into seeded into a T175 cell culture flask (Greiner Bio-One) at $5\times10^5$ cells/ml in RPMI medium (Gibco) supplemented with 10% FCS (Hyclone), L-Penicillin-Streptomycin-Glutamine (1×) (Gibco), 10 mM HEPES (Gibco), 2 mM Sodium pyruvate (Gibco) and 55 µM 2-Mercaptoethanol (Gibco). Thymocytes were incubated at 37° C./5% $CO_2$ in a humidified atmosphere for 48 hours. Subsequently the cells were harvested, collected by centrifugation and resuspended in fresh medium. Thymocytes were counted and stimulated by the addition of 5 µg/ml Phytohemagglutinin M (Sigma-Aldrich, St. Louis, Mo., USA) and 10 ng/ml Phorbol 12-Myristate-13-Acetate (Sigma-Aldrich).

The stimulated thymocytes were added to the macrophages at a ratio of approx. 2:1 (thymocytes:macrophages). After 36 hours of co-cultivation the supernatant of the cells (TSN) was harvested, filtered through a 0.2 µM filter and stored in aliquots at −80° C.
Isolation and Cultivation of Antigen-Specific Ovine B-Cell Pools Suffolk-Merino sheep were immunized several times using a KLH-coupled hapten as immunogen (500 µg dose formulated in an adjuvant). Five days before isolation of B-cells sheep were boosted by a subcutaneous application of the immunogen (500 µg dose per animal formulated in an adjuvant). For isolation of B-cells approx. 150 ml EDTA-blood was taken from the animals and mixed with an equal volume of PBS. The diluted blood was loaded on Leucosep™ tubes (Greiner Bio-One, Frickenhausen, Germany) (20 ml per tube) and centrifuged for 15 min. at 800×g at room temperature. After centrifugation the PBMCs (peripheral blood mononuclear cells) were collected, washed with PBS and counted using a counting chamber.

Following washing with PBS the PBMCs were resuspended in FACS Buffer (PBS/1% BSA) at $5\times10^7$ cells/ml. For positive panning of antigen-specific B-cells, the cells were labeled by incubation with the biotinylated hapten (500 ng/ml) for 30 min. at 4° C. under gentle rotation. Subsequently cells were washed with PBS and resuspended in Labeling Buffer (PBS/2 mM EDTA) at $1\times10^7$ cells per 90 µl. Cells were incubated with magnetic streptavidin microbeads (Miltenyi Biotec, Bergisch-Gladbach, Germany) for 30 min. at 4° C. under gentle rotation (using 10 µl of the beads per 90 µl of cell suspension). After washing with PBS cells were resuspended in MACS Buffer (PBS/1% BSA/2 mM EDTA) at $2\times10^8$ cells/ml and loaded on MACS column (Miltenyi Biotec) equilibrated with MACS buffer. Following washing with MACS buffer the magnet was removed from the column and labeled, antigen-specific cells were eluted in MACS buffer.

For staining of B-cells the eluted cell fraction was washed with PBS and resuspended in FACS Buffer at $2\times10^7$ cells/ml. Cells were stained using a 1:50 diluted FITC-labeled anti-sheep IgG monoclonal antibody (Clone GT-34) (Sigma-Aldrich, St. Louis, Mo., USA) in combination with a 1:10 diluted RPE-labeled anti-sheep CD45R mAb (clone 20.96, AbD Serotec, Düsseldorf, Germany) or RPE-labeled anti-sheep CD21 mAb (clone CC21, AbD Serotec). Cells were incubated with the mAbs for 45 min. at 4° C. under gentle rotation. In control experiments aliquots of the cells were stained with the individual mAbs alone (single staining). Unstained cells served as negative control.

After washing with PBS cells were resuspended in FACS buffer and subjected to cell sorting using a FACS Aria I cell sorter (BD Biosciences, Heidelberg, Germany). Surface IgG $(sIgG)^+CD21^+$ or $sIgG^+CD45R^+$ double positive B-cells were identified and sorted into a 96-well plate (50 cells/well) containing 280 µl medium and γ-irradiated murine thymoma EL4B5 feeder cells (approx. $5\times10^4$ feeder cells/well seeded 24 hours before cell sorting into the plates).

The basal medium was either DMEM (Gibco, Paisley, UK) or IMDM (Gibco) supplemented with 10% FCS (Hyclone, Logan, Utah, USA), L-Penicillin-Streptomycin-Glutamine (1×) (Gibco), 55 µM 2-Mercaptoethanol (Gibco), sheep TSN (1:20 dilution) and heat-killed, formalin-fixed *Staphylococcus aureus* cells (SAC; 1:10,000 dilution) (Pansorbin®, Calbiochem, Darmstadt, Germany). The basal IMDM contained 0.025% Pluronic F-68 (Gibco) in addition to the supplements described above.

In order to evaluate the impact of different stimuli on proliferation and differentiation of ovine B-cells the following compounds were added alone or in combination to the basal medium as indicated in the Figures: 10 ng/ml human IL-4 (Peprotech, Hamburg, Germany), 50 ng/ml human IL-6 (Roche Diagnostics GmbH, Mannheim, Germany), 1 µg/ml *E. coli* derived Lipopolysaccharide (LPS) (Sigma-Aldrich) or 1 µg/ml Phorbol 12-Myristate-13-Acetate (PMA) (Sigma-Aldrich).

B-cells were incubated for 7 to 10 days in the medium at 37° C./5% $CO_2$ in a humidified atmosphere. Subsequently the supernatant of the cells was harvested and the IgG concentration was determined by ELISA as described below.

Isolation and Cultivation of Single Antigen-Specific B-Cells

Sheep PBMCs from immunized animals were isolated as described above. Antigen-specific B-cells were enriched by positive panning using the biotinylated antigen and magnetic streptavidin microbeads (Miltenyi Biotec) as described above. Cells were stained using a 1:50 diluted FITC-labeled anti-sheep IgG monoclonal antibody (Clone GT-34) (Sigma-Aldrich) in combination with a 1:10 diluted RPE-labeled anti-sheep CD21 mAb (AbD Serotec). Cells were incubated with the mAbs for 45 min. at 4° C. under gentle rotation. In control experiments aliquots of the cells were stained with the individual mAbs alone (single staining). Unstained cells served as negative control.

After washing with PBS cells were resuspended in FACS buffer and subjected to cell sorting using a FACS Aria I cell sorter (BD Biosciences). Single $sIgG^+CD21^+$ double positive B-cells were identified and sorted into a 96-well plate (one cell/well) containing 280 µl medium and γ-irradiated murine EL4B5 feeder cells (approx. $5 \times 10^4$ feeder cells/well seeded 24 hours before cell sorting into the plates).

The medium for cultivation of single ovine B-cells was IMDM (Gibco) was supplemented with 10% FCS (Hyclone), L-Penicillin-Streptomycin-Glutamine (1×) (Gibco), 55 µM 2-Mercaptoethanol (Gibco), 0.025% Pluronic F-68 (Gibco), sheep TSN (1:20 dilution), SAC (1:10,000 dilution) (Calbiochem) and 1 µg/ml PMA (Sigma-Aldrich).

B-cells were incubated for 7 to 10 days in the medium at 37° C./5% $CO_2$ in a humidified atmosphere. Subsequently the supernatant of the cells was harvested and the IgG concentration was determined by ELISA as described below Determination of Sheep IgG Concentration by ELISA A biotin-conjugated monoclonal anti-sheep IgG antibody (cat. #213-062-177, Dianova, Hamburg, Germany) was immobilized on a streptavidin coated 96-well plate (MicroCoat, Bernried, Germany). The mAb (100 µl/well) was used at a concentration of 300 ng/ml in PBS/1% RPLA4 (bovine plasma albumin) (Roche Diagnostics GmbH, Mannheim, Germany) and wells were incubated for 1 hour at room temperature (RT) with the diluted mAb. After washing with Wash Buffer (0.9% NaCl/0.05% Tween) the supernatants of the in vitro cultivated B-cells or serial dilutions of purified polyclonal sheep IgG (Roche) were added to the plates and incubated for 1 h at RT. After washing with Wash Buffer wells were incubated with a donkey anti-sheep IgG (H+L) antibody (1:15,000 dilution in PBS/1% RPLA4) labeled with horseradish peroxidase (Dianova, cat. #713-035-147). After incubation for 1 h at RT the plates were washed with Wash Buffer and signals were detected using ABTS solution (Roche) as substrate. Plates were read in a microplate reader at 405 nm (reference wavelength 492 nm). The serial dilutions of purified sheep IgG (0-200 ng/ml) served as standard and were used for calculation of the IgG concentration of the B-cell supernatants.

Determination of Antigen-Specificity of Sheep IgG by ELISA

Biotin-conjugated antigens were immobilized on a streptavidin coated 96-well plate (MicroCoat, Bernried, Germany). The biotinylated antigens (100 µl/well) were used at a concentration of 100-300 ng/ml in PBS/1% RPLA4 (bovine plasma albumin) (Roche Diagnostics GmbH, Mannheim, Germany) and wells were incubated with the diluted antigens for 1 hour at room temperature (RT). After washing with Wash Buffer (0.9% NaCl/0.05% Tween) the supernatants of the in vitro cultivated B-cells or serial dilutions of purified polyclonal sheep IgG (Roche) were added to the plates and incubated for 1 hour at RT. After washing with Wash Buffer wells were incubated with a donkey anti-sheep IgG (H+L) antibody (1:15,000 dilution in PBS/1% RPLA4) labeled with horseradish peroxidase (Dianova, cat. #713-035-147). After incubation for 1 hour at RT the plates were washed with Wash Buffer and signals were detected using ABTS solution (Roche Diagnostics GmbH, Mannheim, Germany) as substrate.

The invention claimed is:

1. A method for improving cell growth of a B-cell or a pool of B-cells for IgG antibody production, the method comprising:
    obtaining from an immunized ovine a B-cell from peripheral blood mononuclear cells or a pool of B-cells enriched from peripheral blood mononuclear cells, and cultivating the B-cell or the pool of B-cells,
    the method being characterized in that the B-cells are ovine IgG positive B-cells which present the surface marker IgG, and the method being further characterized in that the cultivating is performed in the presence of phorbol myristate acetate (PMA),
    thereby improving cell growth of the one or more B-cells; and
    recovering an IgG antibody from the cultivation supernatant.

2. The method of claim 1, wherein the cultivating step is performed in the presence of phorbol myristate acetate (PMA), ovine TSN and feeder cells.

3. The method according to claim 1, wherein the ovine B-cell is a niave or non-mature ovine B-cell.

4. The method of claim 1, wherein the B-cell is an IgG positive and CD45R positive B-cell ($IgG^+CD45R^+$).

5. The method of claim 1, wherein the B-cell is an IgG positive and CD21 positive B-cell ($IgG^+CD21^+$).

* * * * *